US011176753B1

(12) United States Patent
Chakravarthi et al.

(10) Patent No.: US 11,176,753 B1
(45) Date of Patent: Nov. 16, 2021

(54) AUGMENTED REALITY FIELD OF VIEW BASED ON SENSED USER DATA

(71) Applicant: INTERNATIONAL BUSINESS MACHINES CORPORATION, Armonk, NY (US)

(72) Inventors: Divya Kannan Chakravarthi, Wappingers Falls, NY (US); Kriteshwar Kaur Kohli, White Plains, NY (US); Vinod A. Valecha, Pune (IN); John A. Lyons, Ottawa (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/864,353

(22) Filed: May 1, 2020

(51) Int. Cl.
*G06T 19/00* (2011.01)
*G06F 3/01* (2006.01)
*G06K 9/00* (2006.01)
*G06N 20/00* (2019.01)

(52) U.S. Cl.
CPC ............ *G06T 19/006* (2013.01); *G06F 3/011* (2013.01); *G06K 9/00671* (2013.01); *G06N 20/00* (2019.01)

(58) Field of Classification Search
CPC .... G06T 19/006; G06K 9/00671; G06F 3/011
See application file for complete search history.

(56) References Cited

U.S. PATENT DOCUMENTS

| 6,425,764 | B1 | 7/2002 | Lamson | |
|---|---|---|---|---|
| 10,783,800 | B1 * | 9/2020 | Dieker | G09B 19/00 |
| 10,976,806 | B1 * | 4/2021 | Vancamberg | A61B 5/6803 |
| 2010/0070171 | A1 * | 3/2010 | Barbeau | G01C 21/3617 |
| | | | | 701/408 |
| 2010/0178639 | A1 | 7/2010 | Kameyama et al. | |

(Continued)

FOREIGN PATENT DOCUMENTS

CN 2826468 Y 10/2006
WO WO 2017/151778 A1 9/2017

OTHER PUBLICATIONS

North et al., "Effectiveness of Virtual Environment Desensitization in the Treatment of Agoraphobia", Presence, vol. 4, No. 3, Summer 1996 (pp. 346-352).

(Continued)

*Primary Examiner* — Ryan R Yang
(74) *Attorney, Agent, or Firm* — Tihon Poltavets; Kevin P. Radigan; Heslin Rothenberg Farley & Mesiti P.C.

(57) ABSTRACT

User-specific augmentation of a real word field of view viewable through an augmented reality (AR) device is facilitated by a processor(s) receiving image data representative of a real world field of view viewable by a user through the AR device, and receiving sensor data indicative of the user's stress level, which is related, at least in part, to the user's real world field of view viewable through the AR device. The processor(s) processes the image data, based on the user's stress level, to identify one or more stress-inducing elements to be hidden in the real world field of view viewable through the AR device. Further, the processor(s) provides an augmented real world field of view for display to the user through the AR device, where the one or more stress-inducing elements are hidden from the user in the augmented real world field of view.

12 Claims, 12 Drawing Sheets

(56) References Cited

U.S. PATENT DOCUMENTS

2018/0068577 A1     3/2018    Javanbakht
2020/0258480 A1*   8/2020    Bronder .................. G09G 5/38

OTHER PUBLICATIONS

Botella et al., "Clinically Significant Virtual Environments for the Treatment of Panic Disorder and Agoraphobia", Cyber Psychology & Behavior, vol. 7, No. 5, 2004 (pp. 527-535).

Mel et al., "The NIST Definition of Cloud Computing", National Institute of Standards and Technology, Information Technology Laboratory, Special Publication 800-145, Sep. 2011 (pp. 1-7).

Kikhia et al., "Utilizing a Wristband Sensor to Measure the Stress Level for People with Dementia", Sensors, vol. 16, 12, Nov. 24, 2016 (pp. 1-17).

Mori et al., "A Survey of Diminished Reality: Techniques For Visually Concealing, Eliminating, and Seeing Through Real Objects", IPSJ Transactions on Computer Vision and Applications, vol. 9, No. 17, 2017 (pp. 1-14).

Andersen et al., "Augmented Reality Concentration Cubicle", ip.com, IPCOM000249206D, Feb. 9, 2017 (pp. 1-6).

Evegard et al., "Augmented Reality Navigation Interfaces Designed for People with Mild Dementia", (Dissertation), Retrieved from http://urn.kb.se/resolve?urn=urn:nbn:se:kth:diva-232083, Stockholm, Sweden, 2018 (pp. 1-10).

Leatham, Juanita, "AR Apps That Inspire People With Anxiety To Go Outside", VR Insider, Retrieved from https://www.vrfitnessinsider.com/ar-apps-that-inspire-people-with-anxiety-to-go-outside/, published Mar. 10, 2018 (pp. 1-3).

Dahl Tyler, "Real-Time Object Removal in Augmented Reality", (Master's Thesis) California Polytechnic State University, San Luis Obispo, CA, Jun. 2018 (pp. 1-96).

Kennesaw State University, "Professor Using VR to Aid Learning Among Students With Autism", Retrieved from https://www.newswise.com/articles/professor-using-vr-to-aid-learning-among-students-with-autism, published Apr. 10, 2019 (pp. 1-3).

"LookBack—Virtue Health", https://www.virtue.io/lookback/, downloaded Feb. 27, 2020 (2 pages).

* cited by examiner

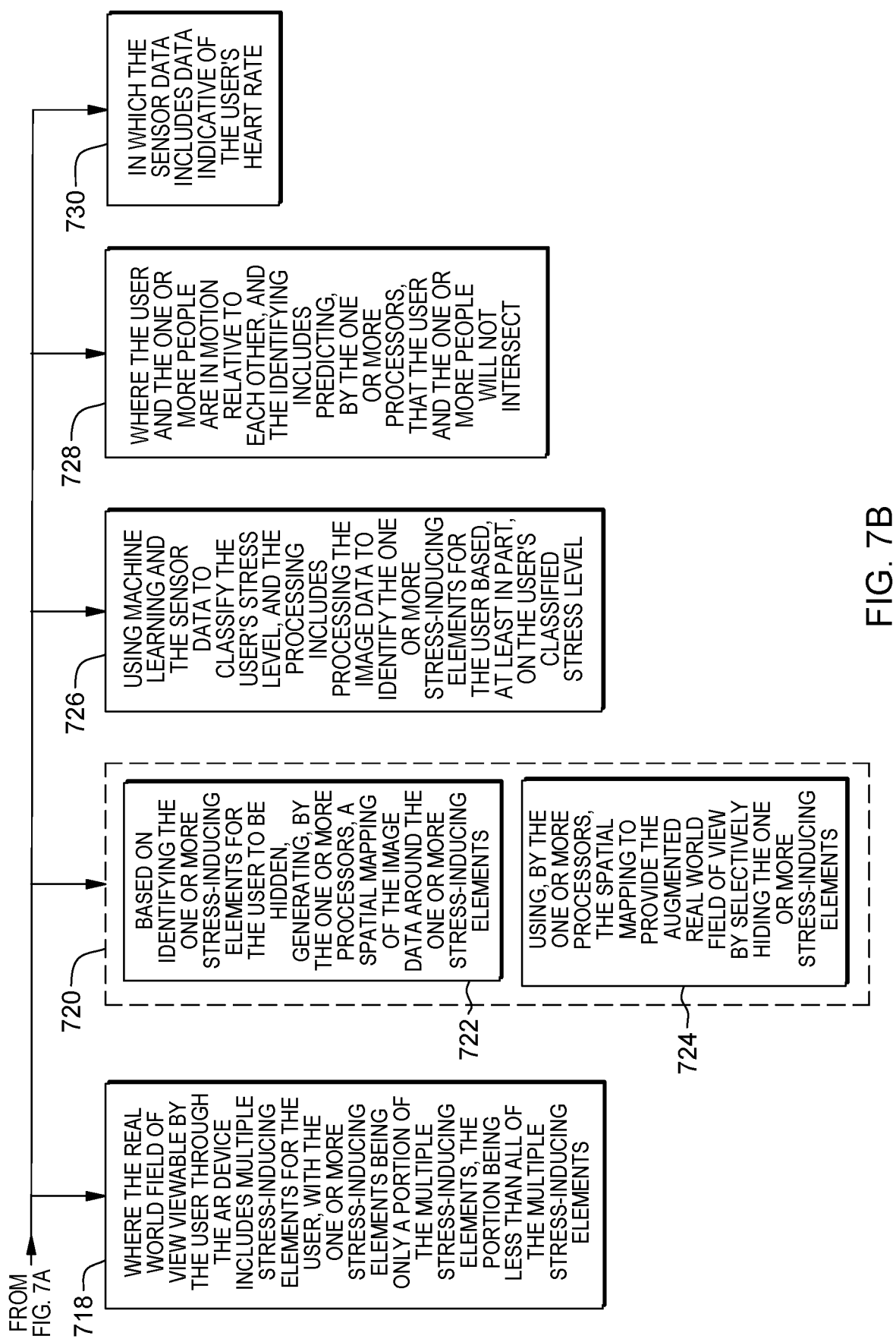

AUGMENTED REALITY FIELD OF VIEW BASED ON SENSED USER DATA

BACKGROUND

Agoraphobia is a type of anxiety disorder in which an individual is anxious in situations or places where the individual perceives that their environment is unsafe, with no easy way to escape. For instance, the individual can fear situations such as using public transportation, being in open or enclosed spaces, standing in line, being in a crowd, or simply being outside their home. An individual with agoraphobia often has a hard time feeling safe in any public place, especially where crowds gather. The individual's anxiety can be so overwhelming that the individual may feel unable to leave their home. Agoraphobia treatment can be challenging, because it often involves confronting the patient's fears. Without treatment, it is uncommon for agoraphobia to resolve. Treatment is typically with a type of counseling referred to as cognitive behavioral therapy (CBT), which is helpful in resolving the disorder for only about half of the individuals counseled.

SUMMARY

Certain shortcomings of the prior art are overcome and additional advantages are provided through the provision, in one or more aspects, of a computer-implemented method, which includes receiving, by one or more processors, image data representative of a real world field of view viewable by a user through an augmented reality (AR) device, and receiving, by the one or more processors, sensor data indicative of a stress level of the user, where the user's stress level is related, at least in part, to the real world field of view viewable by the user through the AR device. Based on the user's stress level, the one or more processors process the image data to identify one or more stress-inducing elements for the user to be hidden in the real world field of view viewable through the AR device. The one or more processors further provide an augmented real world field of view for display to the user through the AR device, where the one or more stress-inducing elements are hidden from the user in the augmented real world field of view viewable by the user through the AR device.

Systems and computer program products relating to one or more aspects are also described and claimed herein. Further, services relating to one or more aspects are also described and can be claimed herein.

Additional features and advantages are realized through the techniques described herein. Other embodiments and aspects of the invention are described in detail herein and are considered a part of the claimed aspects.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIGS. 7A-7B depict a further workflow illustrating certain aspects of one or more embodiments of the present invention;

DETAILED DESCRIPTION

Figure 1:
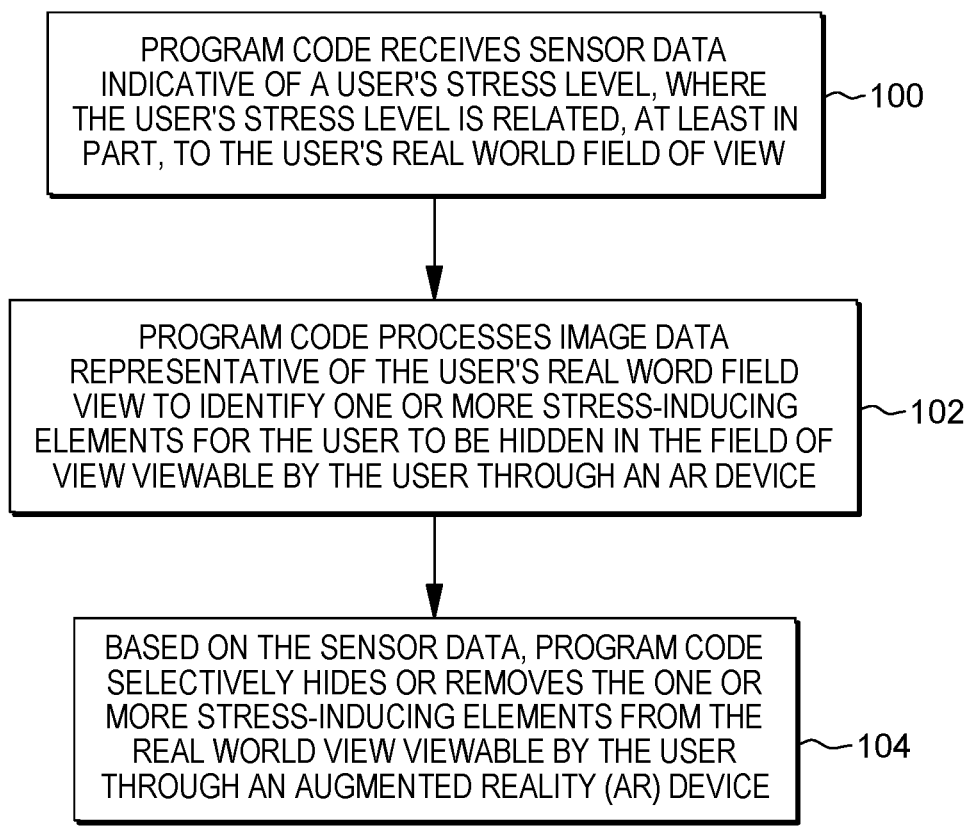
FIG. 1 is a workflow that illustrates certain aspects of some embodiments of the present invention.

The accompanying figures, in which like reference numerals refer to identical or functionally similar elements throughout the separate views, and which are incorporated in and form a part of the specification, further illustrate the present invention and, together with the detailed description, serve to explain aspects of the present invention. Note in this regard that descriptions of well-known systems, devices, processing techniques, etc., are omitted so as not to obscure the invention in detail. It should be understood, however, that the detailed description and this specific example(s), while indicating aspects of the invention, are given by way of illustration only, and not limitation. Various substitutions, modifications, additions, and/or other arrangements, within the spirit or scope of the underlying inventive concepts will be apparent to those skilled in the art from this disclosure. Note further that numerous inventive aspects and features are disclosed herein, and unless inconsistent, each disclosed aspect or feature is combinable with any other disclosed aspect or feature as desired for a particular application of one or more of the concepts disclosed herein.

Note also that illustrative embodiments are described below using specific code, designs, architectures, protocols, layouts, schematics, or tools only as examples, and not by way of limitation. Furthermore, the illustrative embodiments are described in certain instances using particular software, tools, or data processing environments only as example for clarity of description. The illustrative embodiments can be used in conjunction with other comparable or similarly purposed structures, systems, applications, or architectures. One or more aspects of an illustrative embodiment can be implemented in hardware, software, or a combination thereof.

As understood by one skilled in the art, program code, as referred to in this application, can include both software and hardware. For example, program code in certain embodiments of the present invention can include fixed function hardware, but other embodiments can utilize a software-based implementation of the functionality described. Certain embodiments combine both types of program code.

Figure 8:
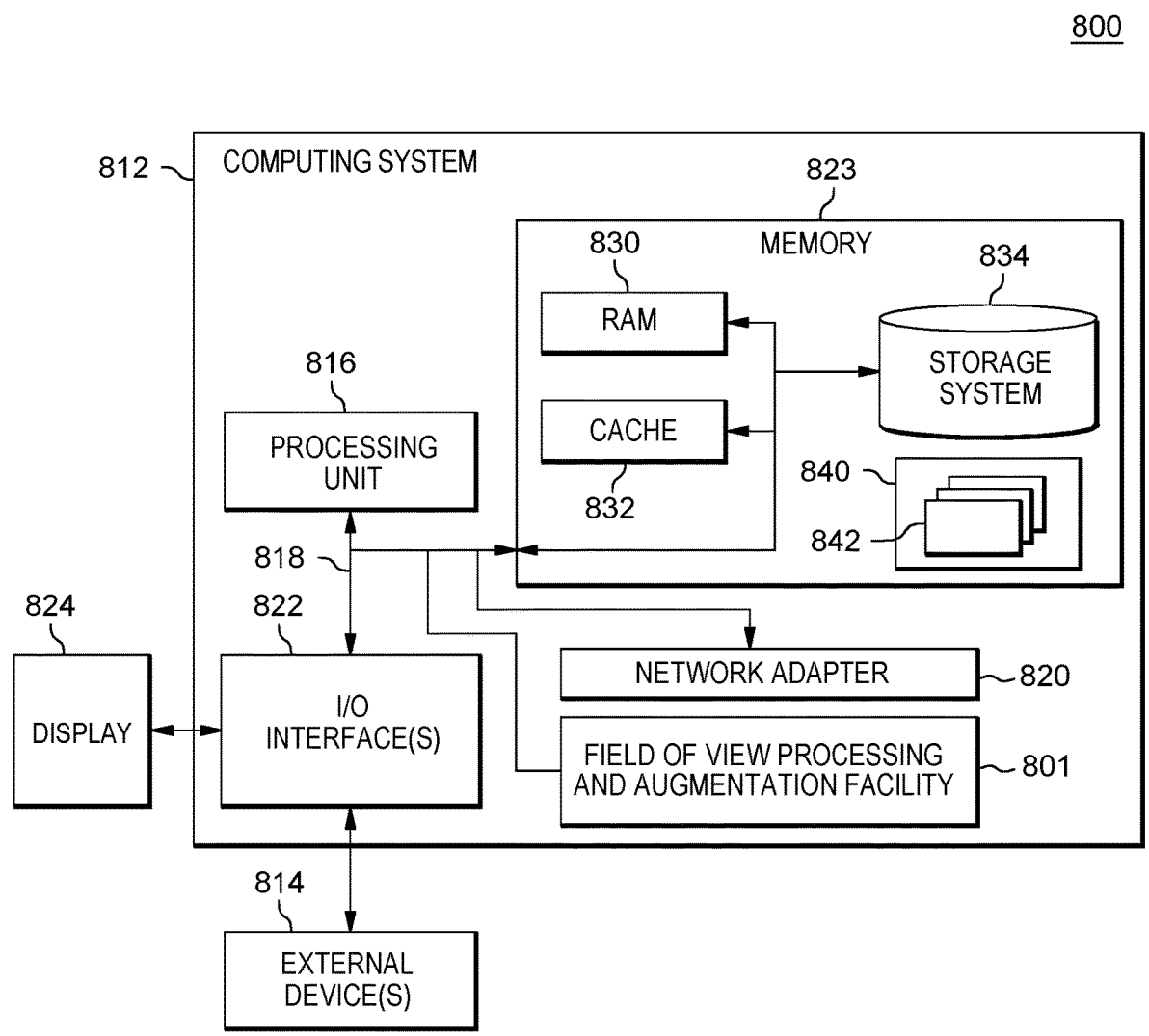
FIG. 8 depicts one embodiment of another computing system to implement, or facilitate implementing, one or more aspects of a field of view processing and augmentation facility, in accordance with one or more aspects of the present invention.

One example of program code, also referred to as one or more programs or program instructions, is depicted in FIG. 8 as program/utility 840, having a set (at least one) of program modules 842, which can be stored in memory 823. As a further example, FIG. 8 depicts additional, or alternative, program code implemented as a field of view processing and augmentation facility or module 801. As a further example, in FIG. 3, program code implementing one or more aspects described herein could be stored or resident in main memory 308, read-only memory 324, disc storage 326, CD-ROM 330, and/or other peripheral devices of computing environment 300.

As noted initially, agoraphobia is a type of disorder in which an individual can become stressed in one or more situations that might cause the individual to feel anxious and trapped. Depending on the individual disorder, stressful situations can include open spaces, public transport, shopping centers, standing in line, or being in a crowd. People with agoraphobia often have a hard time feeling safe in any public space, especially where crowds gather.

To assist in addressing this disorder, disclosed herein, in one or more aspects, is the use of augmented reality (AR) to dynamically modify a real world situational experience of the user by overlapping or hiding one or more stress-inducing elements to the user in the real world field of view viewed by the user through the AR device. For instance, where the user is an agoraphobic patient, or a patient with social anxiety disorder, large crowds are overlaid with other objects, or individuals within the crowd can be removed or hidden entirely from view using spatial mapping techniques, providing the user with a perception of a smaller gathering, personalizing the AR viewable image to reduce the user's anxiety, and making the space feel more open to the user, thereby reducing the user's stress or anxiety. Over time, as the user's condition improves, the field of view processing and augmentation facility can dynamically expose more the of real world field of view to the user based on the user's currently sensed health data to assist in the user's treatment plan.

An augmented reality (AR) device is, for instance, a wearable glass device, or headset-mounted device, with an incorporated, or associated, augmented reality system that provides an interactive experience of a real world environment to a user where objects or elements that reside in the real world can be enhanced or modified by computer-generated perceptual information, including across multiple sensory modalities, if desired. An augogram is a computer-generated image, in whole or in part, used to create an augmented reality field of view. An AR device or system can combine real and virtual worlds, is real-time interactive, and provides accurate 3-D registration of virtual and real objects. The overlaid sensory information can be constructive, that is, additive to the natural environment, or destructive, that is, masking of the natural environment. The experience can be seamlessly interwoven with the physical world such that it is perceived as an immersive aspect of the real environment. In this way, augmented reality can alter the user's ongoing perception of a real world environment.

Advantageously, through a combination of real-time stress level sensing or measurement, and diminished reality techniques using an augmented reality (AR) device/system, a computer-implemented method, system and computer program product are provided herein which allow an individual or user with, for instance, social anxiety or agoraphobia, to function in the real world without fully having addressed their disorder. Over time, the computer-implemented method, system and computer program product disclosed herein allow the individual to resolve their condition by gradually confronting their fears, dependent on the real-time stress level data obtained for the user as the user functions in the real world.

More particularly, embodiments of the present invention include a computer-implemented method, system, and computer program product, where program code executing on one or more processors receives image data representative of a real world field of view viewable by a user through an augmented reality (AR) device, and receives sensor data indicative of a current stress level of the user, where the user's stress level is related, at least in part, to the real world field of view viewable by the user through the AR device. Embodiments of the present invention also include program code executing on one or more processors which processes, based on the user's stress level, the image data to identify one or more stress-inducing elements for the user to be hidden in the real world field of view viewable by the user through the AR device. Further, embodiments of the present invention include program code executing on one or more processors that provides an augmented real world field of view for display to the user through the AR device, where the one or more stress-inducing elements are hidden from the user in the augmented real world field of view viewable through the AR device.

In certain embodiments of the present invention, providing the augmented real world field of view for display to the user through the AR device includes selectively hiding, by the one or more processors, only the identified one or more stress-inducing elements in the augmented real world field of view for display to the user through the AR device.

In one or more embodiments of the present invention, the one or more stress-inducing elements include one or more people in the real world field of view viewable through the AR device. Further, in one embodiment, program code executing on the one or more processors determines that the user and the one or more people are in motion relative to each other, and the identifying includes predicting by the program code that the user and the one or more people will not intersect. In one or more embodiments of the present invention, the program code executing on the one or more processors receives location data for the user to predict whether the user is approaching or in a crowded area, and the processing of the image data is further based on the location data predicting that the user is approaching or in the crowded area.

In certain embodiments of the present invention, the real world field of view viewable by the user through the AR device includes multiple stress-inducing elements for the user, and the one or more stress-inducing elements identified to be hidden are only a portion of the multiple stress-inducing elements viewable by the user through the AR device, with the portion being less than all of the multiple stress-inducing elements.

In one or more embodiments of the present invention, providing the augmented real world field of view for display to the user includes, based on identifying the one or more stress-inducing elements for the user to be hidden, generating by the program code executing on the one or more processors, a spatial mapping of the image data around the one or more stress-inducing elements, and using the spatial mapping to provide the augmented real world field of view by selectively hiding the one or more stress-inducing elements.

In certain embodiments of the present invention, program code executing on one or more processors uses machine learning and the sensor data to classify the user's stress level, and the processing includes processing the image data to identify the one or more stress-inducing elements for the user based, at least in part, on the user's classified stress level.

In one embodiment, the sensor data includes data indicative of the user's heart rate.

Embodiments of the present invention are inextricably tied to computing and provide significantly more than existing approaches to addressing an individual's anxiety disorder. For instance, embodiments of the present invention provide program code executing on one or more processors to exploit the interconnectivity of various systems, as well as to utilize various computing-centric data analysis and handling techniques, in order to receive image data representative of a real world field of view viewable by a user through an augmented reality (AR) device, and receive sensor data indicative of a stress level of the user, where the user's stress level is related, at least in part, the real world field of view viewable by the user through the AR device, and based on the user's stress level (e.g., based on the user's stress level exceeding a threshold), process the image data to identify one or more stress-inducing elements to be hidden and provide an augmented real world field of view for display to the user through the AR device, where the one or more stress-inducing elements are hidden from the user in the augmented real world field of view. Both the interconnectivity of the devices and/or computing systems utilized, and the computer-exclusive data processing techniques utilized by the program code, enable various aspects of the present invention. Further, embodiments of the present invention provide significantly more functionality than existing approaches to treating an individual with an anxiety disorder, by advantageously allowing the individual to continue to function in the real world, while simultaneously addressing the individual's anxiety disorder through conditioning.

In embodiments of the present invention, the program code provides significantly more functionality, including but not limited to: 1) program code that receives image data representative of a real world field of view viewable by a user through an augmented reality (AR) device; 2) program code that receives sensor data indicative of a stress level of the user, where the user's stress level is related, and least in part, to the real world field of view viewable by the user through the AR device; 3) program code that processes, based on the user's stress level, the image data to identify one or more stress-inducing elements for the user to be hidden in the real world field of view viewable through the AR device; and 4) program code that provides an augmented real world field of view for display to the user through the AR device, where the one or more stress-inducing elements are hidden from the user in the augmented real world field of view viewable through the AR device.

By way of example, FIG. 1 depicts one embodiment of a workflow or process illustrating one or more aspects of some embodiments of the present invention. In one or more embodiments of the present invention, program code executing on one or more processors receives sensor data indicative of a user's stress level, where the user's stress level is related, at least in part, the user's real world field of view 100 as viewed through an augmented reality (AR) device, such as AR glasses or an AR headset. For example, the sensor data can be from one or more health measurement or sensor devices worn by or associated with the user, such as a heart rate monitor or smart watch capable of measuring the user's heart rate. Program code executing on the one or more processors processes received image data representative of the user's real world field of view to identify one or more stress-inducing elements for the user to be hidden in the real world field of view viewable by the user through an augmented reality (AR) device 102. In one or more implementations, based on the user's stress level, program code executing on one or more processors selectively hides or removes the one or more stress-inducing elements from the real world field of view viewable by the user through the AR device 104. For instance, in one or more embodiments, only the identified one or more stress-inducing elements are removed from the modified or augmented real world field of view displayed to the user through the AR device.

Note that the particular stress-inducing element to be hidden is dependent on the individual user, and the user's condition being addressed. Agoraphobia, or a social anxiety disorder, is discussed herein in connection with one or more embodiments of the invention, by way of example only. For instance, in one or more implementations, the one or more stress-inducing elements could be one or more animals, such as one or more dogs, cats, etc., or any other stress-inducing element or object for the particular user. Advantageously, the computer-implemented method, system, and program product disclosed herein allow a user to continue to function in the real world by selectively hiding or blocking one or more stress-inducing elements from the augmented real world field of view display to the user through the AR device based on the received sensor data indicative of the user's current stress level. Note also, although described with reference to heart rate, the sensor data could measure other biological characteristics indicative of stress or anxiety, such as blood pressure, perspiration, or breathing.

Figure 2:
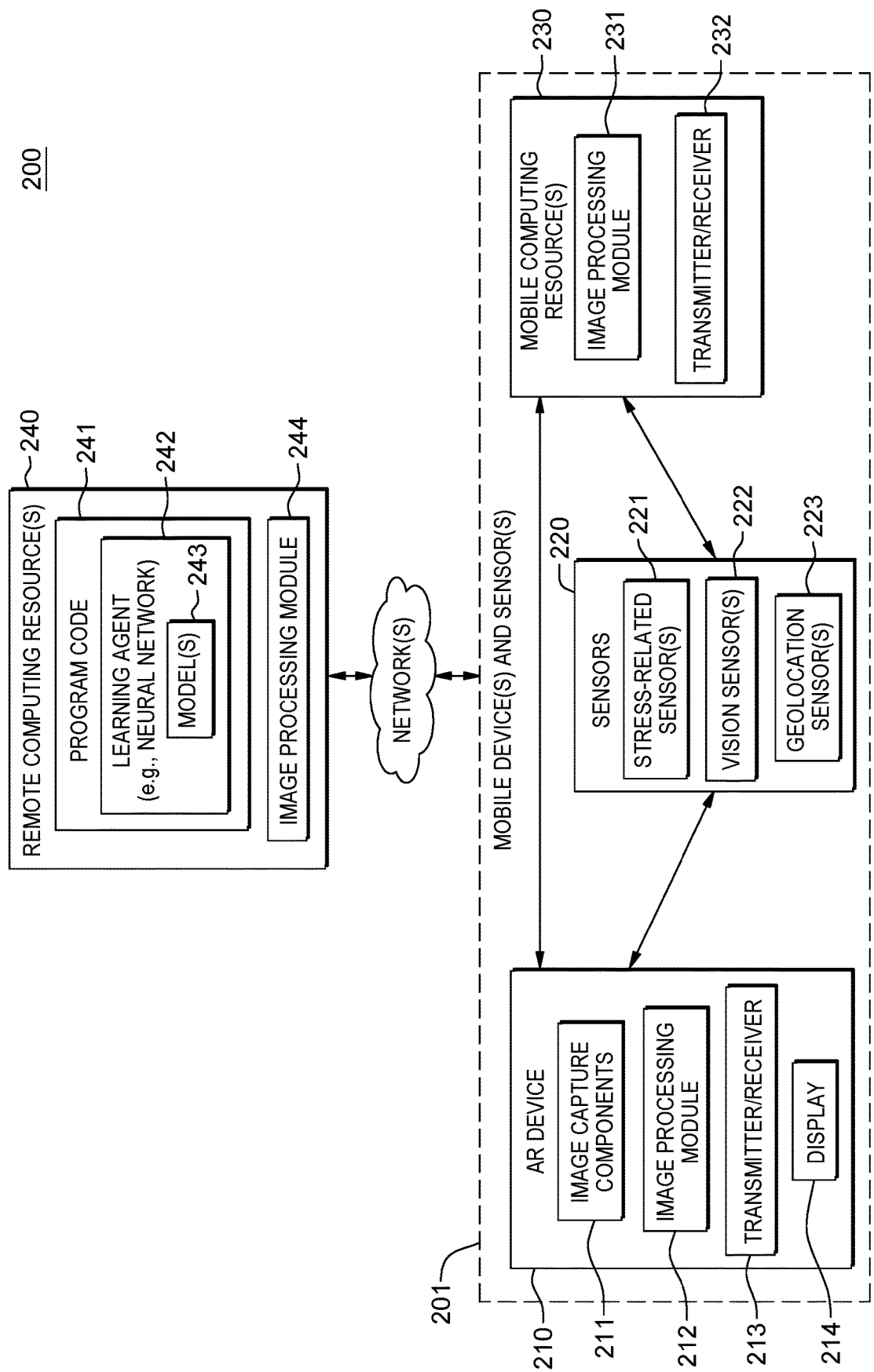
FIG. 2 depicts one embodiment of a system, illustrating certain aspects of an embodiment of the present invention, in accordance with one or more aspects of the present invention.

FIG. 2 depicts one embodiment of a system 200, illustrating certain aspects of an embodiment of the present invention. System 200 includes various computing devices, including one or more mobile devices and one or more sensor(s) 201, such as an augmented reality (AR) device 210, one or more sensors 220, such as sensors worn by or associated with the user of the system, and one or more mobile computing resources 230, such as a smartphone or other mobile computing resource associated with the user. In the embodiment depicted, system 200 also includes one or more remote computing resources 240 in communication with AR device 210, sensors 220 and/or mobile computing resource(s) 230 across one or more networks 205. By way of example, in one or more embodiments, AR device 210, sensor(s) 220, mobile computing resource(s) 230, and remote computing resource(s) 240, can each have a wireless communication capability for communicating data to facilitate processing, as described herein. By way of example, network(s) 205 can be, for instance, a telecommunications network, a local-area network (LAN), a wide-area network (WAN), such as the Internet, or a combination thereof, and can include wired, wireless, fiber-optic connections, etc. The network(s) can include one or more wired and/or wireless networks that are capable of receiving and transmitting data, including image data, sensor data, and location data, such as discussed herein.

By way of example, AR device 210 can include or have associated therewith digital image capture components 211, such as conventional image or video camera components and related sensors. Further, computing resource(s) 210 can include an image processing module 212. Note in this regard that, in the embodiment of FIG. 2, system 200 includes, by way of example, image processing module 212 associated with AR device 210, as well as, or alternatively, image processing module 231 associated with mobile computing resource(s) 230, and image processing module 244 associated with remote computing resource(s) 240. This is one implementation only. In one or more other implementations, the image processing module (or program code) could be associated with only one of the computing resources or AR device, or otherwise located. In one embodiment, image processing module 212 can include image-video-based processing for, for instance, object detection or element detection using conventional detection algorithms. For instance, where people are the element to be detected in the image data, facial recognition code can be used to detect people in the user's field of view. Additionally, AR device 210 includes transmitter and/or receiver logic or circuitry 213, and a display 214 for displaying, for instance, the real world field of view of the user of the system, or an augmented version of the real world field of view, such as disclosed herein. In one or more embodiments, display 214 of AR device 210 can include augmented reality glasses or an augmented reality headset worn by the user.

In the embodiment illustrated, sensors 220 include, by way of example, one or more stress-related sensors 221, one or more vision sensors 222, and one or more geolocation sensors 223. Note that sensors 220 can be associated with or worn by the user, and can be separate from AR device 210 and mobile computing resource(s) 230, or integrated within one or more both of AR device 210 and mobile computing resource(s) 230. In one or more embodiments, stress-related sensor(s) 221 can be, or can include, for instance, a heart rate sensor, blood pressure sensor, perspiration sensor, etc., worn by the user, and which produces sensor data related to or indicative of the user's current level of stress or anxiety. Vision sensor(s) 222 can include, for instance, image capture components and/or object or element recognition software to, for instance, facilitate identifying one or more stress-inducing elements (e.g., people) within image data representative of a real world field of view viewable by the user through AR device 210. Geolocation sensor(s) 223 can be, for instance, a global positioning sensor, to identify a geographic location of a user, and to facilitate correlating that geographic location to an area of historically high-traffic, such as an area that is typically crowded, such as an airport, train station, arena, etc. Further, geolocation sensor(s) 223 and related program code could assist in identifying a currently congested area, such as by identifying the presence of a large number of mobile devices in close proximity, where the devices are associated with different people.

Mobile computing resource(s) 230 can be, for instance, associated with AR device 210, or separate from AR device 210, in which case mobile computing resource(s) 230 can be in wireless communication with AR device 210. By way of example, mobile computing resource(s) 230 can be a smartphone, wireless computer, tablet, personal digital assistant (PDA), a laptop computer, etc., owned by or associated with the user of system 200. In the embodiment illustrated, mobile computing resource(s) 230 can further include an image processing module 231 with program code configured to perform one or more aspects of the image processing and augmentation facility disclosed herein. Mobile computing resource(s) 230 further includes transmitter and/or receiver logic or circuitry 232 for facilitating data transfer from or to AR device 210 and sensor(s) 220, as well as remote computing resource(s) 240.

Note that AR device 210, sensor(s) 220, and mobile computing resource(s) 230 can include additional and/or different components, modules, sensors, sub-systems, etc., without departing from the spirit of the present invention.

Remote computing resource(s) 240 can be, in one or more embodiments, a cloud-based computing resource which includes program code 241 executing on one or more processors to implement one or more aspects of the image processing and augmentation facility disclosed herein. In the embodiment illustrated, program code 241 includes, or has associated therewith, a learning agent 242, such as a neural network, which uses one or more models to provide one or more functional aspects disclosed herein, and an image processing module 244, again, to facilitate implementing one or more aspects of image processing and augmentation as disclosed herein.

Note again that although image processing module 212 is shown associated with AR device 210, image processing module 231 is associated with mobile computing resource(s) 230, and image processing module(s) 244 is associated with remote computing resource(s) 240, this represents one distributed embodiment only of the concepts disclosed. For instance, in one or more other embodiments, AR device 210 may be in communication with mobile computing resource(s) which processes the image and provides the augmented real world field of view for display to the user, and/or can be in communication with remote computing resource(s) 240 for image processing module 244 to process the image data and provide the augmented real world field of view for display to the user through the AR device. Note that one or more of the image processing modules of AR device 210, mobile computing resource(s) 230, and/or remote computing resource(s) 240 can include program code to execute on one or more processors to implement processing as described herein to, for instance, allow an individual with an anxiety disorder to continue to function in the real world, while simultaneously helping the individual in addressing the disorder through conditioning tailored specifically to the user's current level of stress. This is accomplished by selectively overlaying or hiding one or more identified stress-inducing elements for the user within the user's augmented field of view as seen through the AR device.

Figure 3:
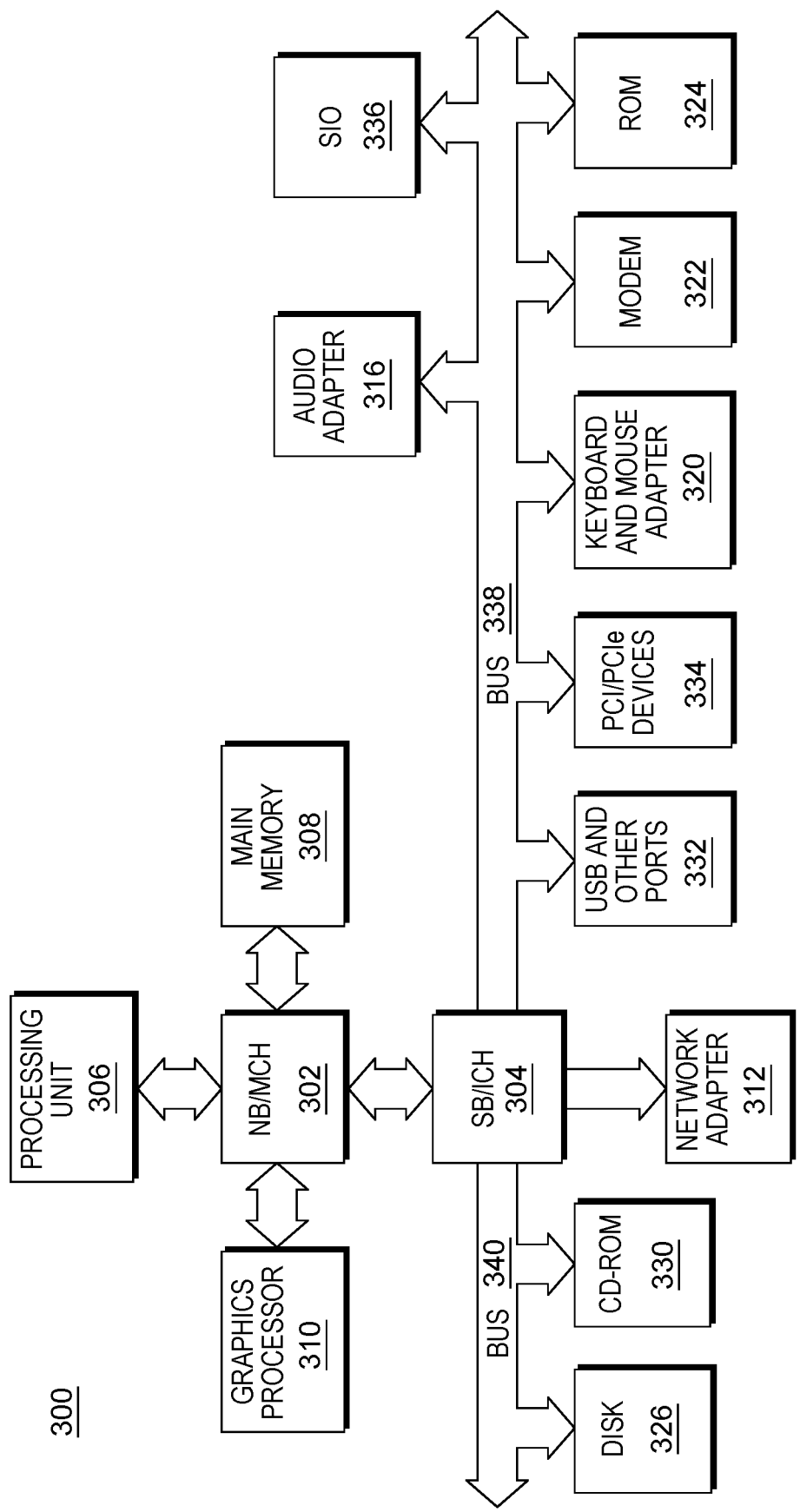
FIG. 3 depicts a block diagram of a computing system which, in one embodiment, can implement one or more aspects of an embodiment of the present invention.

By way of example, FIG. 3 is one example of a processing or computing environment in which illustrative embodiments can be implemented. FIG. 3 is only an example, and not intended to imply limitation with regard to the environment in which different embodiments can be implemented. A particular implementation can have any number of modifications to the depicted environment.

Referring to FIG. 3, a block diagram of a data processing system in which illustrative embodiments can be implemented is shown by way of further example. Data processing system 300 is an example of a computing system, such as AR device 210, mobile computing resource(s) 230, and/or remote computing resource(s) 240 in FIG. 2, in which computer-usable program code or instructions implementing processes such as disclosed herein can be located, in one or more embodiments.

In the depicted example, data processing system 300 includes a hub architecture including a north bridge and memory controller hub (NB/MCH) 302 and a south bridge and input/output (I/O) controller hub (SB/ICH) 304. Processing unit 306, main memory 308, and graphics processor 310 are coupled to north bridge and memory controller hub 302. Processing unit 306 can contain one or more processors and can even be implemented using one or more heterogeneous processor systems. Graphics processor 310 can be coupled to the NB/MCH through an accelerated graphics port (AGP), for example.

In the depicted example, a local area network (LAN) adapter 312 is coupled to south bridge and I/O controller hub 304 and audio adapter 316, keyboard and mouse adapter 320, modem 322, read only memory (ROM) 324, universal serial bus (USB) and other ports 332, and PCI/PCIe devices 334 are coupled to south bridge and I/O controller hub 304 through bus 338, and hard disk drive (HDD) 326 and CD-ROM 330 are coupled to south bridge and I/O controller hub 304 through bus 340. PCI/PCIe devices can include, for example, Ethernet adapters, add-in cards, and PC cards for notebook computers. PCI uses a card bus controller, while PCIe does not. ROM 324 can be, for example, a flash binary input/output system (BIOS). Hard disk drive 326 and CD-ROM 330 can use, for example, an integrated drive electronics (IDE) or serial advanced technology attachment (SATA) interface. A super I/O (SIO) device 336 can be coupled to south bridge and I/O controller hub 304.

An operating system runs on processing unit 306 and coordinates and provides control of various components within data processing system 300 in FIG. 3. The operating system can be a commercially available operating system. An object oriented programming system can run in conjunction with the operating system and provide calls to the operating system from programs or applications executing on data processing system 300.

Instructions for the operating system, the object-oriented programming system, and applications or programs can be located on storage devices, such as hard disk drive 326, and can be loaded into main memory 308 for execution by processing unit 306. The processes of the illustrative aspects discussed herein can be performed by processing unit 306 using computer implemented instructions, which can be located in a memory such as, for example, main memory 308, read only memory 324, or in one or more peripheral devices.

Note that the hardware embodiment depicted in FIG. 3 can vary depending on the desired implementation. Other internal hardware or peripheral devices, such as flash memory, equivalent non-volatile memory, or optical disk drives and the like, can be used in addition to or in place of certain hardware depicted. Also, the processes of the illustrative aspects described herein can be applied to other hardware environments, such as to a multiprocessor data processing system.

In one or more implementations, data processing system 300 can be a mobile electronic device or a server computer resource, and can be generally configured with flash memory to provide non-volatile memory for storing operating system files and/or user-generated data. A bus system can include one or more buses, such as a system bus, an I/O bus and a PCI bus. Of course the bus system can be implemented using any type of communications fabric or architecture that provides for a transfer of data between different components or devices attached to the fabric or architecture. A communications unit can include one or more devices used to transmit and receive data, such as a modem or a network adapter. A memory can be, for example, main memory 308 or a cache such as found in north bridge and memory controller hub 302. A processing unit can include one or more processors or CPUs. Those skilled in the art should note that the depicted system example of FIG. 3, as well as other examples referenced herein, are not meant to imply architectural limitations. As noted, data processing system 300 can be implemented as part of AR device 210, mobile computer resource(s) 230 and/or remote computer resource(s) 240 in FIG. 2, and is presented by way of example only.

The illustrated systems of FIGS. 2-3 can vary depending on the implementation. Other components, hardware or peripheral devices, such as flash memory, equivalent non-volatile memory, or optical disk drives and the like, can be used in addition to or in place of certain components or hardware depicted in FIGS. 2-3. In addition, the processes of the illustrative embodiments can be applied to a multiprocessor data processing system. Examples of additional computing resource(s) or computer system(s) which can implement one or more aspects disclosed herein are also described below with references to FIGS. 8-10. Note also that, depending on the implementation, one or more aspects of the AR device and/or the computing resources can be associated with, licensed by, subscribed to by, etc., a company or organization operating, owning, etc., the AR device/system.

As illustrated in FIG. 2, and as noted above, program code 241 executing on computing resource(s) 240 can include a learning agent which continually learns (in one embodiment) and updates the patterns that form one or more models 243 used, for instance, by the image processing module 244 to, for instance, process sensor data indicative of a stress level of the user, identify one or more stress-inducing elements for a particular user to be hidden in the real world field of view viewable by the user through the AR device, as well as to provide an augmented real world field of view for display to the user through the AR device, where the one or more stress-inducing elements are hidden from the user in the augmented real world field of view viewable through the AR device. In particular, the number of stress-inducing elements to be hidden, location of the stress-inducing elements to be hidden, type of stress-inducing elements to be hidden, etc., can all be customized to the particular user based on the user's disorder and health condition, including the user's current stress level dynamically monitored via the sensor data. Note that these aspects can change over time, for instance, as the user makes improvements to overcoming the disorder. Examples of how the process can be used in one or more applications are described further below, by way of example.

In one or more embodiments, program code 241 executing on remote computing resource(s) 240 applies machine learning algorithms of machine learning agent 242 to generate and train the one or more models 243, which the program code then utilizes to process the sensor data and the image data, and to provide the augmented real world field of view for display to the user through the AR device, as described herein. In an initialization or learning stage, program code 241 can train the algorithm(s) based on patterns for the given user of the AR device/system. Note again that this is one embodiment only. In one or more other embodiments, the machine learning agent and models could run on or be associated with mobile computing resource(s) 230 and/or AR device 210.

Figure 4:
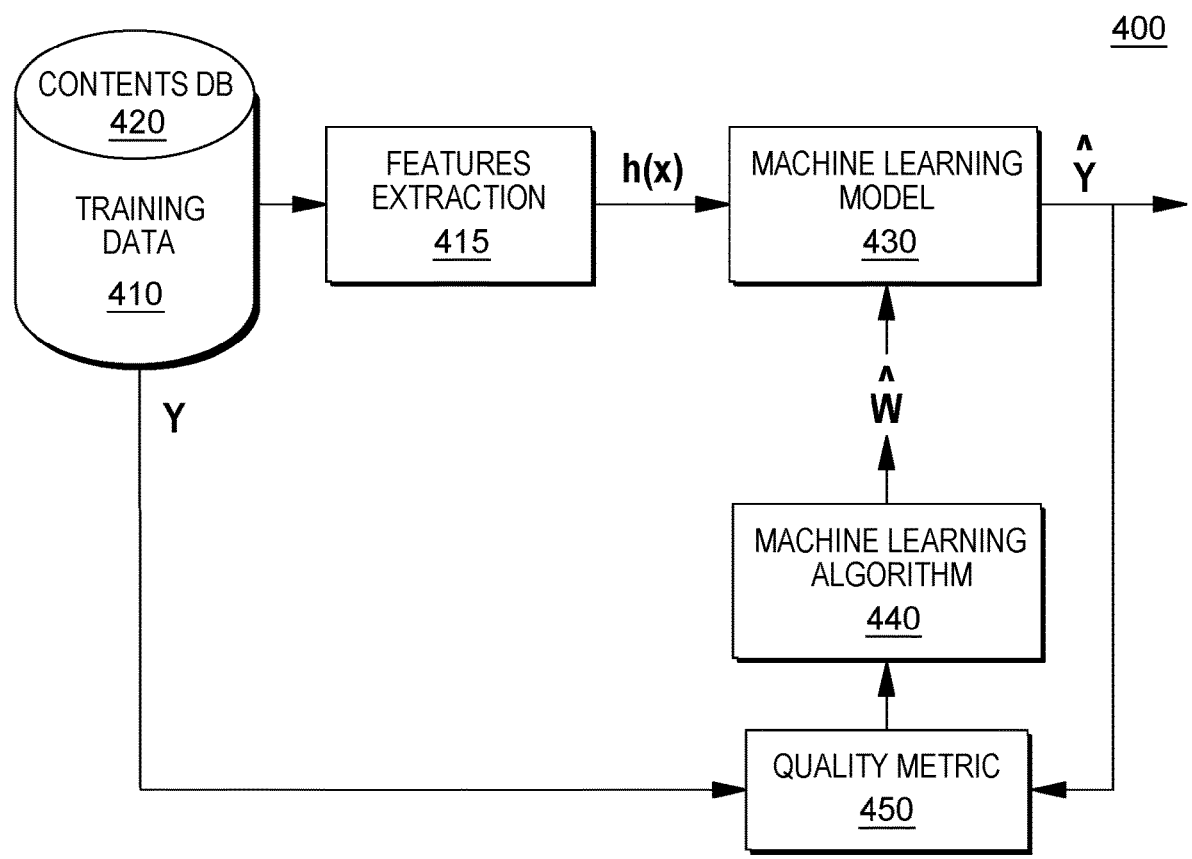
FIG. 4 illustrates various aspects of some embodiments of the present invention.

FIG. 4 is an example machine-learning training system 400 that can be utilized to perform machine-learning, such as described herein. Training data 410 used to train the model in embodiments of the present invention can include a variety of types of data, such as data generated by the AR device and/or sensors. Program code, in embodiments of the present invention, can perform machine-learning analysis to generate data structures, including algorithms utilized by the program code to perform the image processing and augmentation facility, as disclosed herein. Machine-learning (ML) solves problems that cannot be solved by numerical means alone. In this ML-based example, program code extracts various features/attributes from training data 410, which can be stored in memory or one or more databases 420. The extracted features 415 are utilized to develop a predictor function, h(x), also referred to as a hypothesis, which the program code utilizes as a machine-learning model 430. In identifying machine-learning model 430, various techniques can be used to select features (elements, patterns, attributes, etc.), including but not limited to, diffusion mapping, principle component analysis, recursive feature elimination (a brute force approach to selecting features), and/or a random forest, to select the attributes related to the user's condition, and/or to the image processing and augmentation. Program code can utilize a machine-learning algorithm 440 to train machine-learning model 430 (e.g., the algorithms utilized by the program code), including providing weights for conclusions, so that the program code can train any predictor or performance functions included in the machine-learning model 440, such as whether the user is likely to intersect with one or more stress-inducing element(s) based on determined trajectories. The conclusions can be evaluated by a quality metric 450. By selecting a diverse set of training data 410, the program code trains the machine-learning model(s) 440 to identify and weight various attributes (e.g., features, patterns) that correlate to enhance performance of the machine-learning implemented by the computing resource(s) and/or the AR device.

The model(s) used by each respective AR device and/or computing resource(s) can be self-learning, as program code updates the model(s) based on feedback received during performance of the stress level evaluation, image processing, and/or image augmentation, as described herein. For instance, as the user's condition improves, and the sensor data indicates that the user's stress level is lower, a fewer number of the stress-inducing elements, such as a fewer number of people, can be hidden from the user in the augmented real world field of view presented to the user through the AR device.

In some embodiments of the present invention, the program code executing on the respective computing resource(s) of system 200 (FIG. 2) utilizes existing machine-learning analysis tools or agents to create, and tune, each respective model, based, for instance, on data obtained, for instance, from the AR device, or the sensors.

Some embodiments of the present invention can utilize IBM Watson® as learning agent. IBM Watson® is a registered trademark of International Business Machines Corporation, Armonk, N.Y., USA. In embodiments of the present invention, the respective program code can interface with IBM Watson application programming interfaces (APIs) to perform machine-learning analysis of obtained data. In some embodiments of the present invention, the respective program code can interface with the application programming interfaces (APIs) that are part of a known machine-learning agent, such as the IBM Watson® application programming interface (API), a product of International Business Machines Corporation, to determine impacts of data on an operational model, and to update the respective model, accordingly.

In some embodiments of the present invention, certain of the APIs of the IBM Watson API include a machine-learning agent (e.g., learning agent) that includes one or more programs, including, but not limited to, natural language classifiers, Retrieve-and-Rank (i.e., a service available through the IBM Watson® developer cloud that can surface most-relevant information from a collection of documents), concepts/visualization insights, tradeoff analytics, document conversion, natural language processing, and/or relationship extraction. In an embodiment of the present invention, one or more programs can be provided to analyze data obtained by the program code across various sources utilizing one or more of, for instance, a natural language classifier, Retrieve-and-Rank APIs, and tradeoff analytics APIs. In operation, the program code can collect and save machine-learned data used by the machine-learning agent.

In some embodiments of the present invention, the program code utilizes a neural network to analyze collected data relative to a user to generate the operational model(s). Neural networks are a programming paradigm which enable a computer to learn from observational data. This learning is referred to as deep learning, which is a set of techniques for learning in neural networks. Neural networks, including modular neural networks, are capable of pattern (e.g., state) recognition with speed, accuracy, and efficiency, in situations where data sets are multiple and expansive, including across a distributed network, including but not limited to, cloud computing systems. Modern neural networks are non-linear statistical data modeling tools. They are usually used to model complex relationships between inputs and outputs, or to identify patterns (e.g., states) in data (i.e., neural networks are non-linear statistical data modeling or decision making tools). In general, program code utilizing neural networks can model complex relationships between inputs and outputs and identify patterns in data. Because of the speed and efficiency of neural networks, especially when parsing multiple complex data sets, neural networks and deep learning provide solutions to many problems in multi-source processing, which the program code, in embodiments of the present invention, can accomplish when managing machine-learned data sets between devices.

In general, the image processing and augmentation facilities disclosed herein use augmented reality to simplify, via an augmented reality device, the real world field of view viewable by a user so that, for instance, a user with social anxiety disorder, sees fewer people within the user's viewable environment than are actually there. In one or more embodiments, any person within the field of view of the user whose path is unlikely to cross the user's path can be digitally edited out in the augmented real world field of view displayed to the user through the AR device, or can be overlaid with another object, creating a more calming environment for the user to see. This process is implemented dynamically, using the systems disclosed herein, in response to sensor data from sensors worn by the user. In this manner, the amount of alternation to the user's viewable environment is increased or decreased according to the user's current level of stress or anxiety. Advantageously, real-time anxiety-reducing content is delivered to the user through the AR device using the image processing and augmentation facility disclosed herein. For instance, a real-time reduction in the number of people in the user's field of view can be achieved where the individual user has a fear of large crowds. Further, displayed content can be modified dynamically whenever sensor data indicates a change in stress or anxiety in the user, all while allowing the user to operate in the real world. In this manner, the user is able to gradually be reintroduced to the real environment as their stress levels drop. In one or more embodiments, sensor data and machine learning are used to detect an elevated stress level, for instance, above one or more predetermined thresholds, and to take action to alter or augment the user's real world field of view viewable through the AR device. Through the combination of real-time stress level measurement and diminished reality AR techniques, the system allows the user with social anxiety or agoraphobia to function in public, while also conditioning the user to overcome the disorder.

As a specific example, an individual user may suffer from a social anxiety disorder, but need to go out in public to run errands. Public shopping centers present a challenge for the individual due to the large number of people present, and the individual's fear of having to interact with strangers or casual acquaintances. The individual makes use of the system disclosed herein, which combines one or more sensors to dynamically measure the user's level of stress, and an augmented reality headset to provide assistance to the user. As the user enters the shopping center, sensors in the system track people within the user's field of view through the AR device, and calculate their trajectory, along with the user's trajectory, to determine probability that trajectories might intersect. If the system detects that the user is experiencing an elevated level of stress, and the probability that one or more people within the shopping center have a trajectory unlikely to intersect with the user's, for instance, below a configurable threshold, then the system automatically removes those people from the user's augmented field of view viewable through the AR device. People whose trajectory might intersect with the user's trajectory would remain in view to avoid potential collision. The system can further make use of the user's measured stress levels to determine how many people to remove. Thus, as the user becomes more used to crowds, and the user's stress level lowers in the presence of crowds, the system will make fewer adjustments in the augmented real world field of view that the user sees, for instance, removing fewer people as the user's anxiety level lowers, or more people as the user's anxiety level increases.

Figure 5:
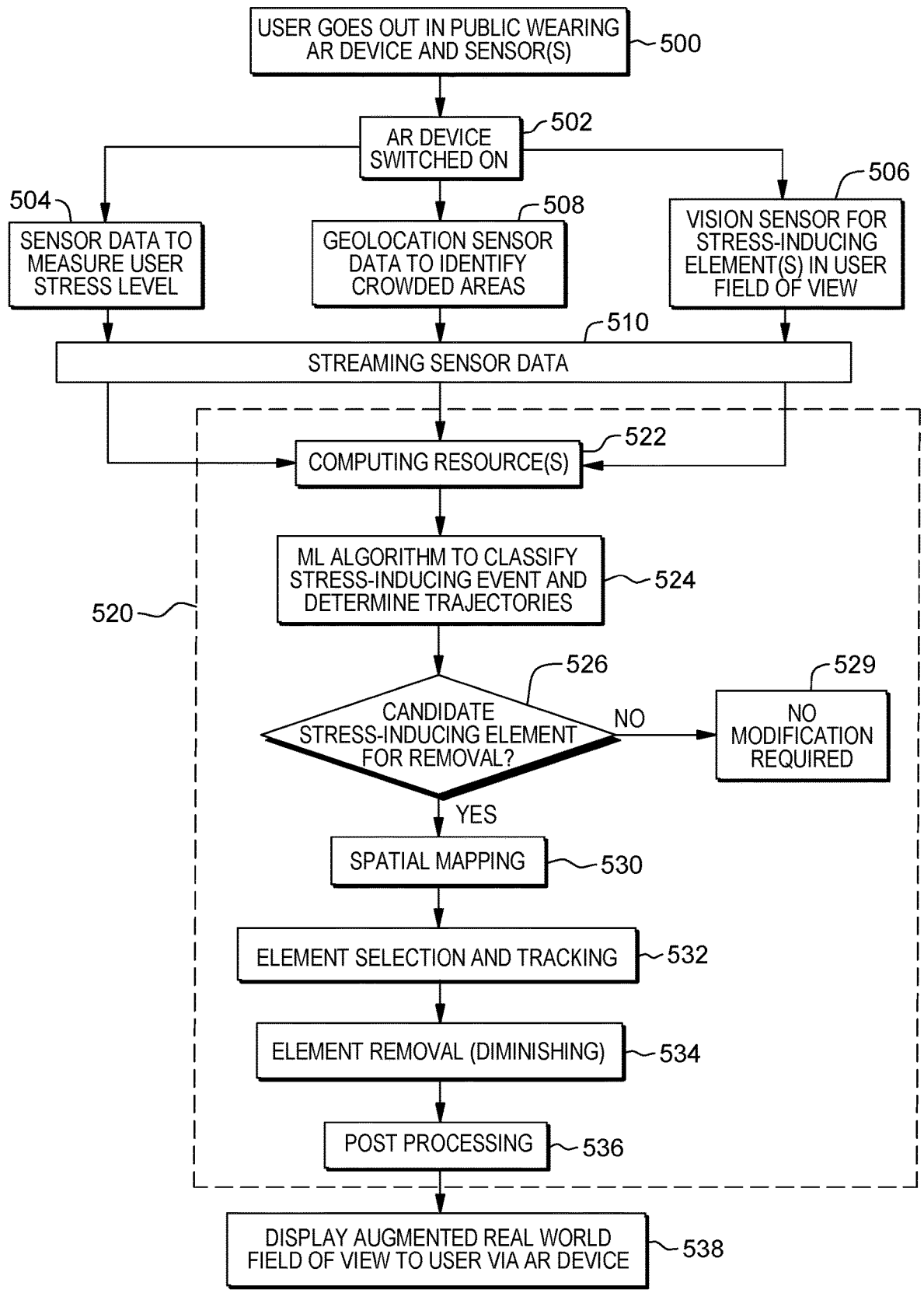
FIG. 5 is a further workflow that illustrates certain aspects of some embodiments of the present invention.

FIG. 5 depicts one detailed implementation of image processing and augmentation, in accordance with one or more aspects of the present invention. In FIG. 5, a user goes out in public wearing the AR device and associated sensors 500, with the AR device being switched on 502, and the sensors collecting data. In the embodiment of FIG. 5, the sensors include sensor data to measure the user's stress level 504, as well as vision sensors to identify stress-inducing elements in the user's path 506, and a geolocation sensor to provide data to assist in identifying crowded areas 508. The sensor data can be provided as streaming sensor data 510 to one or more computing resources 522. In one or more embodiments, the image processing and augmentation facility 520 includes one or more machine learning algorithms to, for instance, classify a stress-inducing event of the user, determine and identify one or more stress-inducing elements in the user's field of view, and determine trajectories of the one or more stress-inducing elements 524. For instance, streaming sensor data is passed to one or more machine learning algorithms to, for instance, predict potentially anxiety-causing situations for the user. Heart rate monitoring, geolocation data, traffic data, and vision sensor data, can all be used as time-series features in an LSTM or RNN, which continuously updates predictions of a user's propensity to have a high-stress or anxiety event. Continuous determination of stress or anxiety levels can be used, and the number of stress-inducing elements can be reduced, as the user's stress level reduces. For instance, LSTM predictions can be gathered throughout the use of the augmented reality device/system, and as the user's level of anxiety is reduced, the amount of diminished reality displayed to the user by the AR device can also be reduced.

As illustrated in FIG. 5, processing determines whether there are one or more candidate stress-inducing elements for removal 526. If "no", then there is no modification, or no further modification, to the real world field of view viewable by the user through the augmented reality device 529. Assuming that there are one or more stress-inducing elements in the user's field of view to be removed, then spatial mapping of the environment surrounding the one or more stress-inducing elements to be removed can be employed 530. This can be done through a mesh-mapping system that is in-built in standard AR devices. Region tracking with 3-D positions can then be performed through simultaneous localization and mapping (SLAM) techniques 532. Existing APIs for augmented reality systems help manage spatial mapping of an environment, as well as performing post-processing operations on the spatial mapping. In one or more implementations, stress-inducing element tracking can be automatic due to the SLAM being performed during the spatial mapping stage. SLAM continually determines, for instance, the camera's position relative to the origin of the environment, and all 3-D locations are mapped relative to the origin as well. Once an object or element has been selected, its 3-D location within the spatial mapping is all that is needed to locate the object per frame. Processing can then perform element removal or diminishing 534. For instance, in-painting can be used, which relies on the idea that patterns are common in nature and often repeated. By repeating nearby patterns in front of the selected region, the element will appear to vanish. A neural network can also be used to learn and repeat patterns from similar images to provide a realistic diminished result. Post-processing 536 can then be performed to provide the augmented real world field of view image to the user's AR display 536. The augmented real world field of view is then displayed to the user via the AR device 538.

Figure 6A:
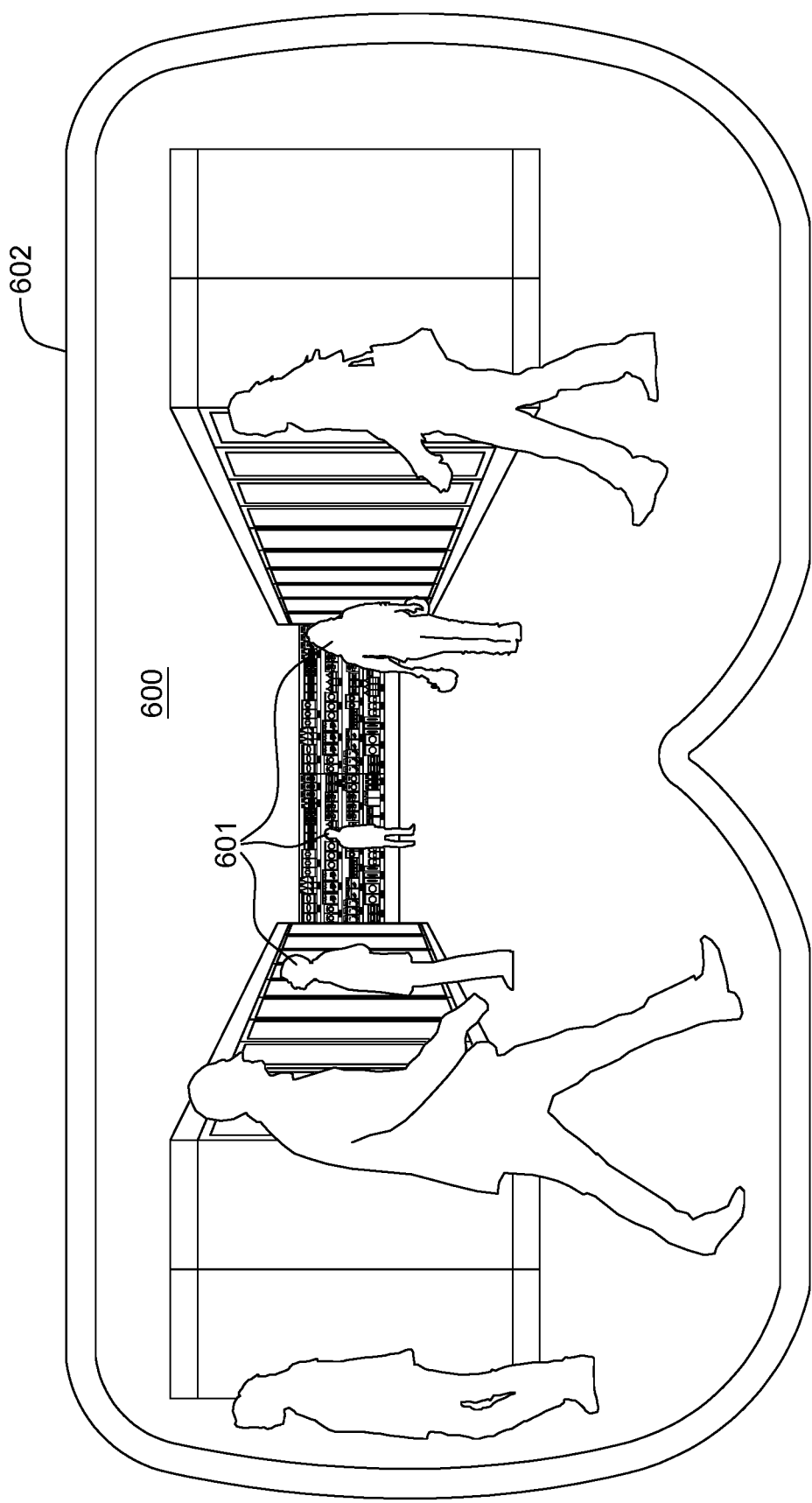
FIGS. 6A & 6B depict one embodiment of a real world field of view viewable through an AR device, and an augmented real world field of view viewable through the AR device, respectively, in accordance with one or more aspects of the present invention.
Figure 6B:
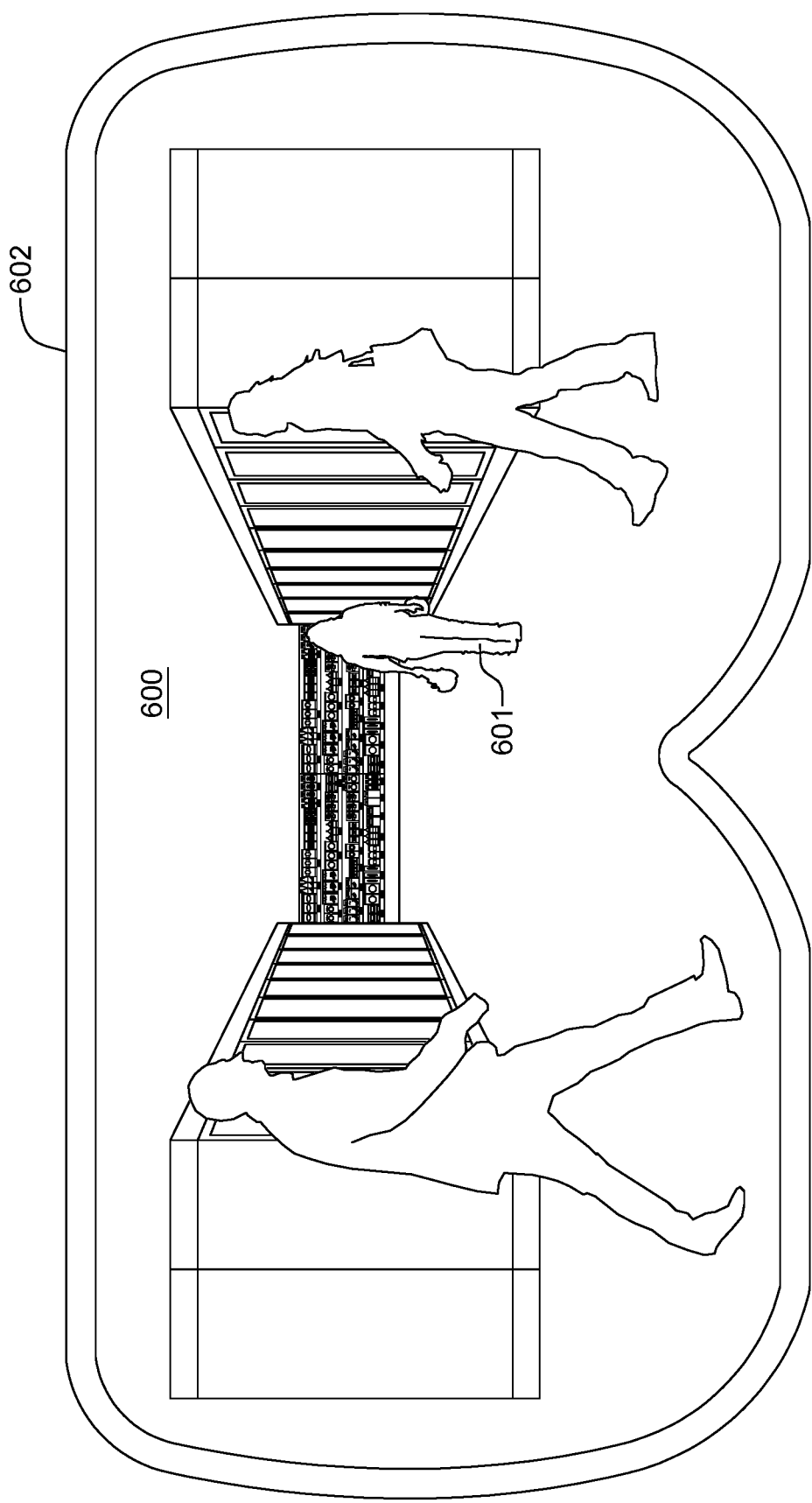

FIGS. 6A & 6B depict one embodiment of a real world field of view 600 viewable through an AR device 602 which includes one or more stress-inducing elements 601, that is, one or more people in the case of a user with a social anxiety disorder. In these figures, FIG. 6A represents the actual real world field of view without any augmentation, while FIG. 6B depicts an augmented real world field of view seen by the user through the augmented reality device, where multiple stress-inducing elements (multiple people in this example) have been removed or hidden from the user's view, while others remain. The ones remaining may be selected or identified to remain, since machine learning predicts there is a possibility or probability that the user's path may intersect with, or come close to the paths of, those remaining individuals.

Figure 7A:
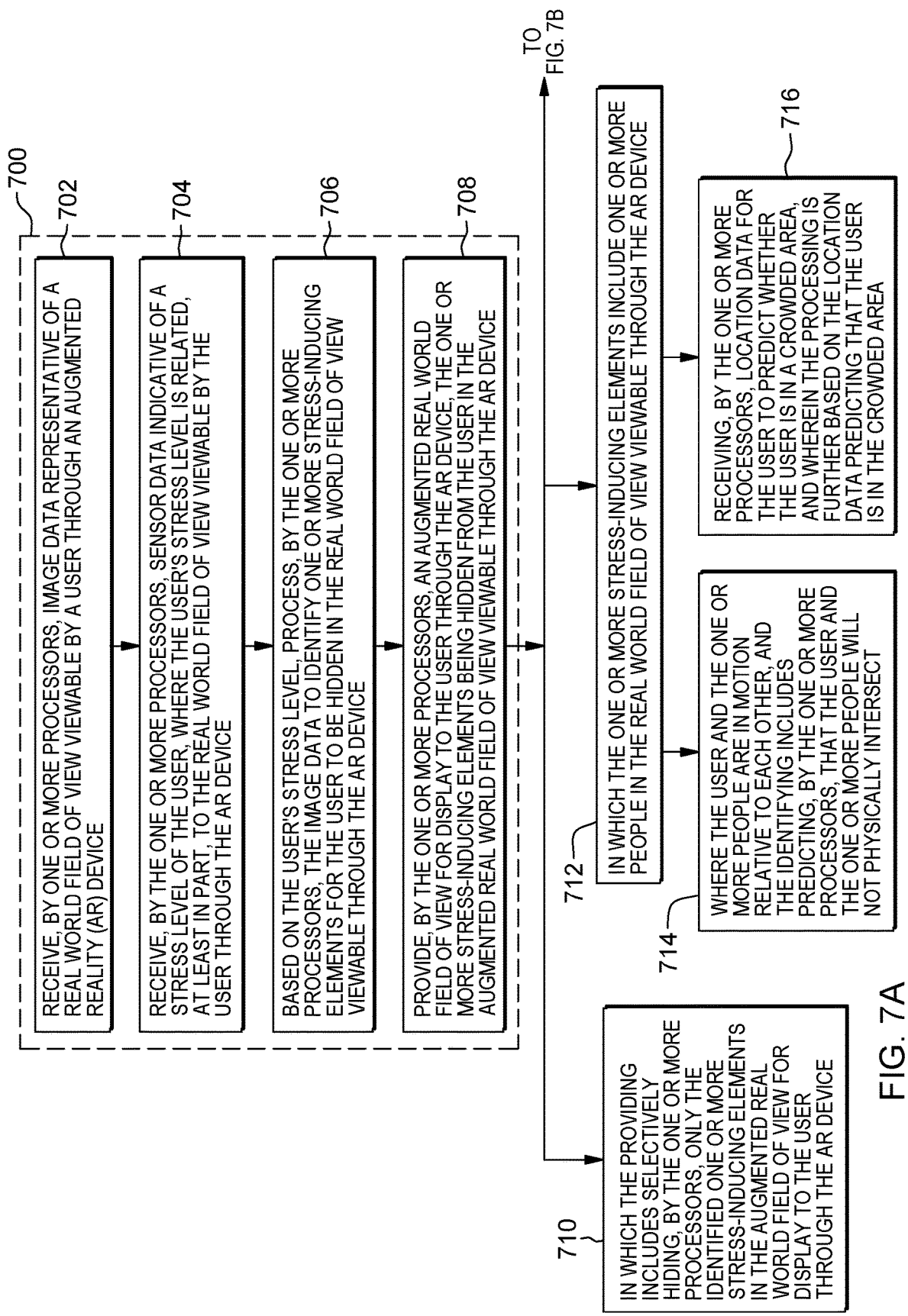

FIGS. 7A-7B depict a further embodiment of program code processing, in accordance with one or aspects of the present invention.

Referring collectively to FIGS. 7A & 7B, program code executing on one or more processors implements a process 700 which includes receiving, by one or more processors, image data representative of a real world field of view viewable by a user through an augmented reality (AR) device 702, and receiving, by the one or more processors, sensor data indicative of a stress level of a user, where the user's stress level is related, at least in part, to the real world field of view viewable by the user through the AR device 704. Based on the user's stress level, the one or more processors process the image data to identify one or more stress-inducing elements for the user to be hidden in the real world field of view viewable through the AR device 706. The one or more processors provide an augmented real world field of view for display to the user through the AR device, where the one or more stress-inducing elements are hidden from the user in the augmented real world field of view viewable through the AR device 708.

In one or more embodiments, providing the augmented real world field of view for display includes selectively hiding, by the one or more processors, only the identified one or more stress-inducing elements in the augmented real world field of view for display to the user through the AR device 710.

In certain embodiments, the one or more stress-inducing elements include one or more people in the real world field of view viewable through the AR device 712. In one embodiment, where the user and one or more people are in motion relative to each other, the identifying includes predicting, by the one or more processors, that the user and the one or more people will not intersect 714. In one or more embodiments, the process also includes receiving, by the one or more processors, location data for the user to predict whether the user is approaching a crowded area, and the processing is further based on the location data resulting in a prediction that the user is approaching a crowded area 716.

In one or more implementations, the real world field of view viewable by the user through the AR device includes multiple stress-inducing elements for the user, with the one or more stress-inducing elements being only a portion of the multiple stress-inducing elements, the portion being less than all of the multiple stress-inducing elements 718.

In one or more embodiments, providing the augmented real world field of view for display further includes a process 720, which includes generating, based on identifying the one or more stress-inducing elements to be hidden, a spatial mapping of the image data around the one or more stress-inducing elements 722, and using the spatial mapping to provide the augmented real world field of view by selectively hiding the one or more stress-inducing elements 724.

In one or more embodiments, the process further includes using machine learning and the sensor data to classify the user's stress level, and the processing includes processing the image data to identify the one or more stress-inducing elements for the user based, at least in part, on the user's classified stress level 726.

In one or more embodiments, the user and the one or more stress-inducing elements are in motion relative to each other, and the identifying includes predicting, by the one or more processors, that the user and the one or more stress-inducing elements will not intersect 728.

In one embodiment, the sensor data includes data indicative of the user's heart rate 730.

Further exemplary embodiments of a computing environment to implement one or more aspects of the present invention are described below with reference to FIGS. 8-10.

By way of further example, FIG. 8 depicts one embodiment of a computing environment 800, which includes a computing system 812. Examples of well-known computing systems, environments, and/or configurations that may be suitable for use with computer system 812 include, but are not limited to, a server, a desktop computer, a work station, a wireless computer, a handheld or laptop computer or device, a mobile phone, a programmable consumer electronic device, a tablet, a personal digital assistant (PDA), and the like.

Computing system 812 can be described in the general context of computer system-executable instructions, such as program modules, being executed by a computer system. Generally, program modules include routines, programs, objects, components, logic, data structures, and so on that perform particular tasks or implement particular abstract data types.

As depicted in FIG. 8, computing system 812, is shown in the form of a general-purpose computing device. The components of computing system 812 can include, but are not limited to, one or more processors or processing units 816, a system memory 823, and a bus 818 that couples various system components including system memory 823 to processor 816.

In one embodiment, processor 816 may be based on the z/Architecture offered by International Business Machines Corporation, or other architectures offered by International Business Machines Corporation or other companies.

Bus 818 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing system 812 can include a variety of computer system readable media. Such media may be any available media that is accessible by computing system 812, and it includes both volatile and non-volatile media, removable and non-removable media.

System memory 823 can include computer system readable media in the form of volatile memory, such as random access memory (RAM) 830 and/or cache memory 832. Computing system 812 can further include other removable/non-removable, volatile/non-volatile computer system storage media. By way of example only, storage system 834 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media could be provided. In such instances, each can be connected to bus 818 by one or more data media interfaces. As described below, memory 823 can include at least one program product having a set (e.g., at least one) of program modules or code that are configured to carry out the functions of embodiments of the invention.

Program/utility 840, having a set (at least one) of program modules 842, can be stored in memory 832 by way of example, and not limitation, as well as an operating system, one or more application programs, other program modules, and program data. Each of the operating system, one or more application programs, other program modules, and program data or some combination thereof, can include an implementation of a networking environment. Program modules 842 generally carry out the functions and/or methodologies of embodiments of the invention as described herein. Alternatively, a field of view processing and augmentation facility, module, logic, etc., 801 can be provided within computing environment 812, as disclosed herein.

Computing system 812 can also communicate with one or more external devices 814 such as a keyboard, a pointing device, a display 824, etc.; one or more devices that enable a user to interact with computing system 812; and/or any devices (e.g., network card, modem, etc.) that enable computing system 812 to communicate with one or more other computing devices. Such communication can occur via Input/Output (I/O) interfaces 822. Still yet, computing system 812 can communicate with one or more networks such as a local area network (LAN), a general wide area network (WAN), and/or a public network (e.g., the Internet) via network adapter 820. As depicted, network adapter 820 communicates with the other components of computing system, 812, via bus 818. It should be understood that although not shown, other hardware and/or software components could be used in conjunction with computing system 812. Examples, include, but are not limited to: microcode, device drivers, redundant processing units, external disk drive arrays, RAID systems, tape drives, and data archival storage systems, etc.

One or more aspects may relate to or use cloud computing.

It is understood in advance that although this disclosure includes a detailed description on cloud computing, implementation of certain teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

A cloud computing node can include a computer system/server, such as the one depicted in FIG. 8. Computer system/server 812 of FIG. 8 can be practiced in distributed cloud computing environments where tasks are performed by remote processing devices that are linked through a communications network. In a distributed cloud computing environment, program modules may be located in both local and remote computer system storage media including memory storage devices. Computer system/server 812 is capable of being implemented and/or performing any of the functionality set forth hereinabove.

Figure 9:
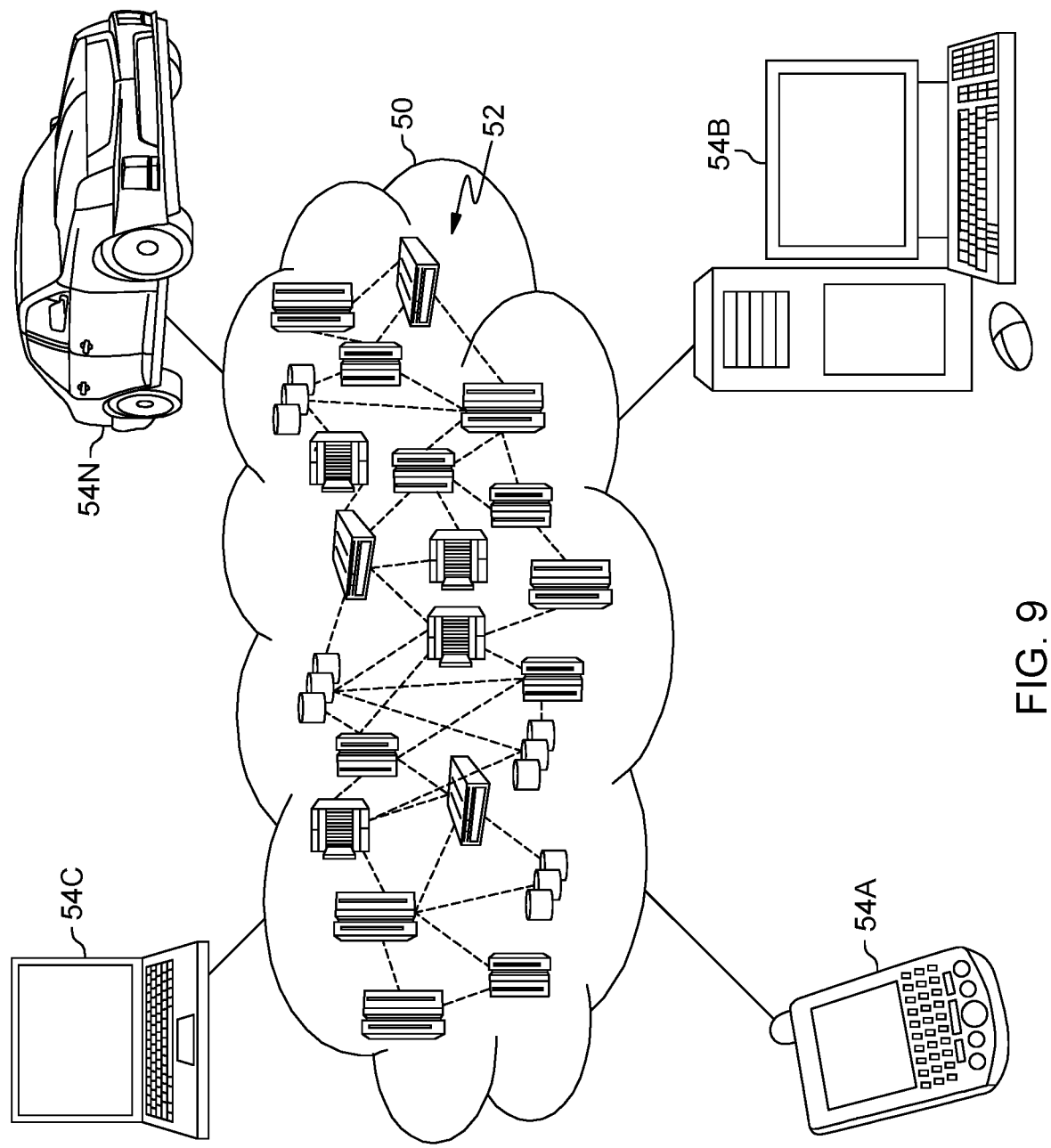
FIG. 9 depicts an embodiment of a cloud computing environment which can facilitate implementing, or be used in association with, certain aspects of an embodiment of the present invention.

Referring now to FIG. 9, illustrative cloud computing environment 50 is depicted. As shown, cloud computing environment 50 can comprise one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 9 are intended to be illustrative only and that computing nodes 10 and cloud computing environment 50 can communicate with any type of computerized device over any type of network and/or network addressable connection (e.g., using a web browser).

Figure 10:
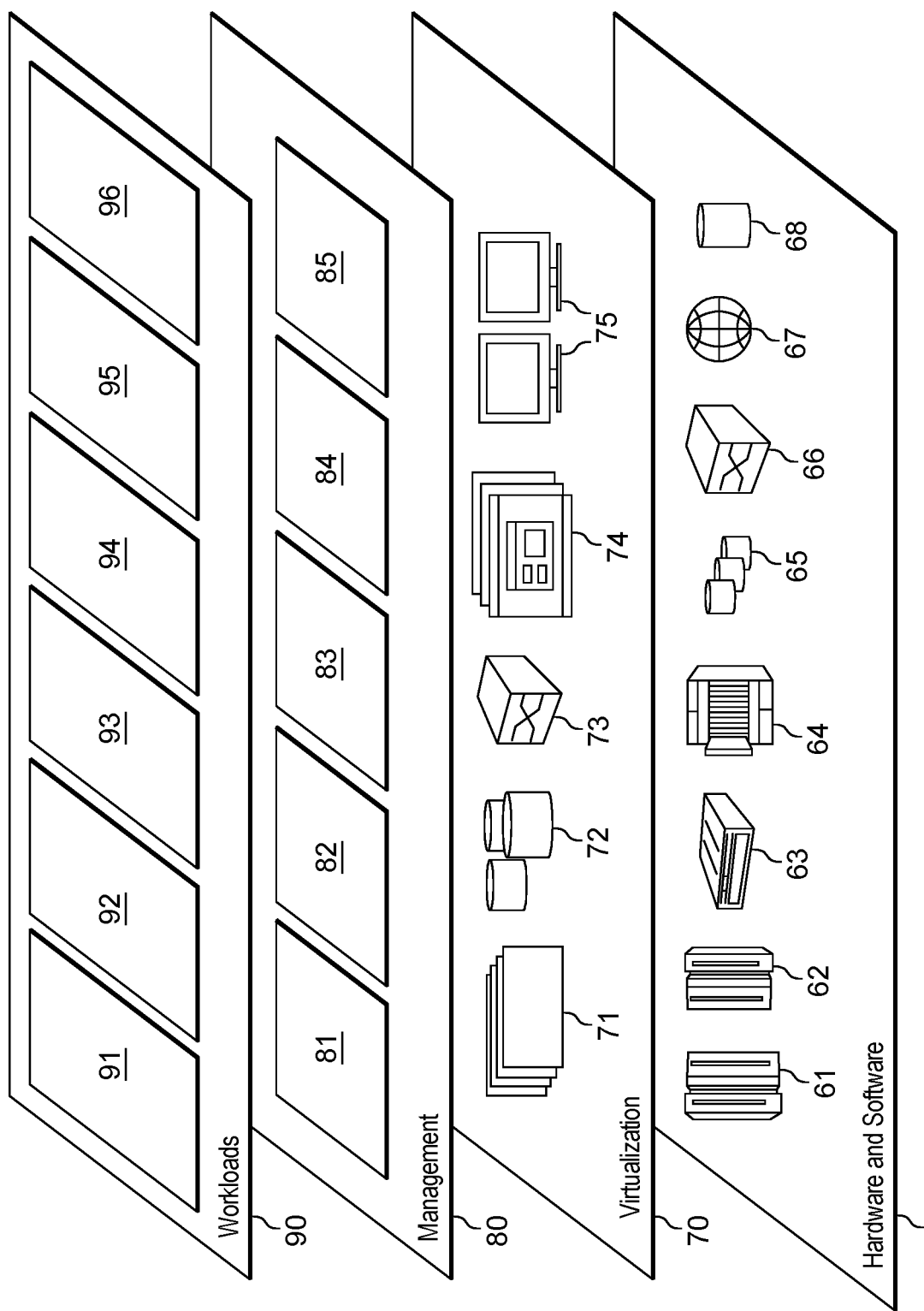
FIG. 10 depicts abstraction model layers according to an embodiment of the present invention.

Referring to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and field of view and augmentation processing 96.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN)

or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, computing environments of other architectures can be used to incorporate and use one or more embodiments. Further, different instructions, instruction formats, instruction fields and/or instruction values may be used. Many variations are possible.

Further, other types of computing environments can benefit and be used. As an example, a data processing system suitable for storing and/or executing program code is usable that includes at least two processors coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A computer-implemented method comprising:
   receiving, by one or more processors, image data on a real world field of view viewable by a user through an augmented reality (AR) device;
   receiving, by the one or more processors, sensor data indicative of a stress level of the user, where the user's stress level is related, at least in part, to the real world field of view viewable by the user through the AR device;
   based on the user's stress level, processing, by the one or more processors, the image data to:
      identify an element in the real world field of view inducing stress for the user, the user and the element being in motion relative to each other;
      predict, by the one or more processors, that the user and the element may intersect;
      identify another element in the real world field of view inducing stress for the user, the user and the other element being in motion relative to each other; and
      predict, by the one or more processors, that the user and the other element will not intersect; and
   providing, by the one or more processors, an augmented real world field of view for display to the user through the AR device, where the element is not hidden from the user in the augmented real world field of view viewable through the AR device, and the other element is hidden from the user in the augmented real world field of view viewable through the AR device.

2. The computer-implemented method of claim 1, wherein the element and the other element each comprise one or more people in the real world field of view viewable through the AR device.

3. The computer-implemented method of claim 1, further comprising receiving, by the one or more processors, location data for the user to predict whether the user is approaching a crowded area, and wherein the processing is further based on the location data predicting that the user approaching the crowded area.

4. The computer-implemented method of claim 1, wherein the providing comprises:
   based on identifying the other element for the user to be hidden, generating, by the one or more processors, a spatial mapping of the image data around the other element; and
   using, by the one or more processors, the spatial mapping to provide the augmented real world field of view by selectively hiding the other element.

5. The computer-implemented method of claim 1, further comprising using machine learning and the sensor data to classify the user's stress level, and the processing comprises processing the image data to identify the element and the other element based, at least in part, on the user's classified stress level.

6. The computer-implemented method of claim 1, wherein the sensor data comprises data indicative of the user's heart rate.

7. A system comprising:
   a memory;
   one or more processors in communication with the memory; and
   program instructions executable by the one or more processors via the memory to perform a method comprising:
      receiving, by the one or more processors, image data on a real world field of view viewable by a user through an augmented reality (AR) device;
      receiving, by the one or more processors, sensor data indicative of a stress level of the user, where the user's stress level is related, at least in part, to the real world field of view viewable by the user through the AR device;
      based on the user's stress level, processing, by the one or more processors, the image data to:
         identify an element in the real world field of view inducing stress for the user, the user and the element being in motion relative to each other;
         predict, by the one or more processors, that the user and the element may intersect;
         identify another element in the real world field of view inducing stress for the user, the user and the other element being in motion relative to each other; and
         predict, by the one or more processors, that the user and the other element will not intersect; and
      providing, by the one or more processors, an augmented real world field of view for display to the user through the AR device, where the element is not hidden from the user in the augmented real world field of view viewable through the AR device, and the other element is hidden from the user in the augmented real world field of view viewable through the AR device.

8. The system of claim 7, wherein the element and the other element each comprise one or more people in the real world field of view viewable through the AR device.

9. The system of claim 7, wherein the providing comprises:
   based on identifying the other element for the user to be hidden, generating, by the one or more processors, a spatial mapping of the image data around the other element; and
   using, by the one or more processors, the spatial mapping to provide the augmented real world field of view by selectively hiding the other element.

10. The system of claim 7, further comprising using machine learning and the sensor data to classify the user's stress level, and the processing comprises processing the image data to identify the element and the other element based, at least in part, on the user's classified stress level.

11. A computer program product comprising:
a computer-readable storage medium having computer-readable code embodied therein, the computer-readable code being executable by one or more processors to cause the one or more processors to:
  receive, by the one or more processors, image data on a real world field of view viewable by a user through an augmented reality (AR) device;
  receive, by the one or more processors, sensor data indicative of a stress level of the user, where the user's stress level is related, at least in part, to the real world field of view viewable by the user through the AR device;
  based on the user's stress level, process, by the one or more processors, the image data to:
    identify an element in the real world field of view inducing stress for the user, the user and the element being in motion relative to each other;
    predict, by the one or more processors, that the user and the element may intersect;
    identify another element in the real world field of view inducing stress for the user, the user and the other element being in motion relative to each other; and
    predict, by the one or more processors, that the user and the other element will not intersect; and
  provide, by the one or more processors, an augmented real world field of view for display to the user through the AR device, where the element is not hidden from the user in the augmented real world field of view viewable through the AR device, and the other element is hidden from the user in the augmented real world field of view viewable through the AR device.

12. The computer program product of claim 11, wherein the element and the other element each comprise one or more people in the real world field of view viewable through the AR device.

\* \* \* \* \*